US008303646B2

(12) United States Patent
Hansen et al.

(10) Patent No.: US 8,303,646 B2
(45) Date of Patent: Nov. 6, 2012

(54) CONFORMABLE STENT STRUCTURE AND METHOD OF MAKING SAME

(75) Inventors: Palle M. Hansen, Bjaeverskov (DK); Per Hendriksen, Herlufmagle (DK)

(73) Assignee: Cook Medical Technologies LLC, Bloomington, IN (US)

( * ) Notice: Subject to any disclaimer, the term of this patent is extended or adjusted under 35 U.S.C. 154(b) by 162 days.

(21) Appl. No.: 12/729,829

(22) Filed: Mar. 23, 2010

(65) Prior Publication Data
US 2010/0241215 A1 Sep. 23, 2010

(30) Foreign Application Priority Data
Mar. 23, 2009 (GB) .................................... 0904962.8

(51) Int. Cl.
*A61F 2/06* (2006.01)
(52) U.S. Cl. ..................................................... 623/1.18
(58) Field of Classification Search .................. 606/108, 606/194, 200; 623/1.15–1.19, 1.1–1.14
See application file for complete search history.

(56) References Cited

U.S. PATENT DOCUMENTS

| 5,449,373 | A | * | 9/1995 | Pinchasik et al. | ............. | 606/198 |
| 5,545,210 | A | * | 8/1996 | Hess et al. | .................... | 128/898 |
| 5,992,020 | A |   | 11/1999 | Minegishi et al. | | |
| 6,527,799 | B2 |   | 3/2003 | Shanley | | |
| 6,626,935 | B1 |   | 9/2003 | Ainsworth et al. | | |
| 6,652,576 | B1 |   | 11/2003 | Stalker | | |
| 6,772,479 | B2 | * | 8/2004 | Hinkley et al. | .................. | 16/225 |
| 6,923,829 | B2 | * | 8/2005 | Boyle et al. | ................... | 623/1.18 |
| 6,997,947 | B2 |   | 2/2006 | Walak et al. | | |
| 6,998,060 | B2 |   | 2/2006 | Tomonto | | |
| 2003/0208263 | A1 |   | 11/2003 | Burmeister et al. | | |
| 2004/0093017 | A1 |   | 5/2004 | Chanduszko | | |
| 2004/0102837 | A1 |   | 5/2004 | Boyle et al. | | |
| 2005/0049690 | A1 |   | 3/2005 | Boismier et al. | | |

FOREIGN PATENT DOCUMENTS

| EP | 0830853 | 3/1998 |
| EP | 1138280 | 10/2001 |
| EP | 1859825 A2 | 11/2007 |
| EP | 2052701 | 4/2009 |
| WO | 02100298 A1 | 12/2002 |
| WO | 03002037 | 1/2003 |
| WO | 03002037 A1 | 1/2003 |
| WO | 2004043221 A2 | 5/2004 |
| WO | 20070134321 | 11/2007 |
| WO | 2009002820 A2 | 12/2008 |
| WO | PCT/US2010/028327 | 7/2010 |

* cited by examiner

*Primary Examiner* — Ryan Severson
*Assistant Examiner* — Ashley Cronin
(74) *Attorney, Agent, or Firm* — Brinks Hofer Gilson & Lione

(57) ABSTRACT

A stent (10) is provided with a plurality of stent rings (12) formed of a plurality of interconnected struts (14). Adjacent stent rings (12) are coupled to one another by a plurality of tie bars (16). Within each tie bar (16) there is provided a hinge (36) which facilitates the curving of the stent (10) in its longitudinal direction and minimizes the generation of returning force to a non-curved configuration by the stent (10). The hinge could, for example, be formed by heat treating a portion of the tie bar (16). This arrangement is particularly suitable for stents or other medical devices intended to be placed in delicate vessels, such as cerebral vessels.

16 Claims, 2 Drawing Sheets

CONFORMABLE STENT STRUCTURE AND METHOD OF MAKING SAME

FIELD OF THE INVENTION

The present invention relates to a conformable stent structure for an implantable medical device and to a method of making such a structure. The invention is particularly suitable for stents but is equally applicable to stent grafts, vena cava filters, occlusion devices and other implantable medical devices which include a stented component or part.

BACKGROUND ART

Stents and other stented implantable medical devices have been used for many years to treat a number of vascular medical conditions. Stents in common use are either of the self-expandable type, made for example of a shape memory material such as Nitinol, or separately expandable, such as by balloon expansion.

Stents and other stented structures are designed to fit within the vasculature of the patient and need to be appropriate for the size and shape of the lumen. For this purpose, they must be conformable and must not be of a nature that they can apply against the vessel walls forces which could damage or adversely affect the functionality of the vessel or of other organs nearby. In the case of self-expanding stents, for example, these will tend to return towards their memory shape and thus will impart a force on any regions of the vessel wall which deform the stent away from its memorised shape. Such force is beneficial in some instances. For example, the radial expansion force generated when the stent is radially compressed assists in holding the stent in position in the lumen and, in the case of a stent graft, ensures in maintaining a proper seal between the implantable medical device and the lumen wall. However, in other instances, this force is a hindrance. For cases in which the medical device is located in a curved lumen, for instance, the force generated by the device can cause stress on the lumen by urging this into an unnatural straightened configuration or by reducing the flexure of the lumen during movement of the patient or of the patient's organs.

It has been known to provide stents with variable flexure characteristics in order to improve the longitudinal deflection properties of the stent, for example by having a part of the stent which is more flexible. In an example, a middle section of the stent could be made less rigid in order to give the stent improved longitudinal flexibility.

There are numerous known methods for increasing the flexibility of parts a stented structure. One method involves making the struts and/or other parts thinner than other parts of the structure. Another method enables making these parts of a softer material. It is similarly possible to heat treat a part of the shape memory structure in order to raise its transition temperature, for example to significantly above body temperature. So doing causes that part to remain in its martensitic phase when in the patient and to remain malleable, so as to deform in a quasi-elastic manner, with no or little tendency to return to its original shape.

There is a problem, however, with increasing the flexibility of a part of a stent in a manner as described above. A more flexible, or weaker, part of a stent structure will lose radial and/or longitudinal strength, in dependence upon the component or components which are made more flexible. In the case where only the tie bars or other components which are intended to provide longitudinal flexibility to the structure are made more flexible, although the structure will be able to conform better to the shape of the patient's lumen, these will not provide longitudinal strength to that stent. This can cause the stent to fail to provide the necessary support to the lumen and possibly to fail to retain its position in the lumen, with possible risk of migration of the medical device.

Prior art stent structures are disclosed in U.S. Pat. No. 6,652,576, U.S. Pat. No. 6,997,947, U.S. Pat. No. 5,992,020, U.S. Pat. No. 6,527,799, U.S. Pat. No. 6,998,060 and EP-1,859,825.

SUMMARY OF THE INVENTION

The present invention seeks to provide an improved stent, an improved medical device and an improved method of making a medical device such as a stent.

According to an aspect of the present invention, there is provided an implantable medical device including a stented structure formed of a plurality of stent sections coupled together by one or more coupling elements, the coupled stent sections extending in at least one longitudinal direction, wherein the or at least one of the coupling elements is hinged to allow for said coupled stent sections to pivot around the hinge so as to flex the stented structure in said longitudinal direction.

In a preferred embodiment, the hinge forms a part of the coupling element.

Most preferably, the or each coupling element extends substantially in said at least one longitudinal direction of the medical device.

The provision of a hinged element enables the stented structure to bend in its longitudinal direction and thus gives longitudinal flexibility to the medical device. The provision of a hinge avoids the need for providing softer zones in the structure, as are included in the prior art devices discussed above, and thus avoids the loss of longitudinal stability of the stent structure. Hinges allow flexibility and yet retain the longitudinal strength of the structure.

In the preferred embodiment the hinge or hinges provide substantially no return force when folded. This is particularly advantageous for delicate vessels such as cerebral vessels and the vessels inside other organs.

Advantageously, the stented structure is made of shape memory material such as Nitinol. The provision of hinges in a self-expanding structure provide the advantages known with such structures but without the disadvantages of a device which will generate a straightening force on the vessel walls.

With a stented structure formed from shape memory material, the hinge or hinges could be formed of zones of increased flexibility within the shape memory material itself, which zones enable pivoting of the coupling element or elements relative to the stent rings which it couples together.

Such zone or zones of increased flexibility forming the hinge or hinges could be thinner than the remainder of the coupling element, could be formed of a softer material or a material exhibiting a smaller shape memory return force. In the preferred embodiment, the zone or zones of increased flexibility are zones which have been heat treated to give them a higher transition temperature, for example of 40 to 60° C. or more. Raising the transition temperature of a hinged zone above normal human temperature ensures that the hinge will remain in its more malleable, martensitic, phase even when the medical device is in situ in a patient, whereas the remainder of the coupling element, having a lower transition temperature in the region of 25 to 30° C., will be heated through its transition temperature to regain its shape memory characteristics when the device is in situ in a patient.

In the preferred embodiment, the hinge or hinges are part of the coupling element. In an embodiment, the hinge represents around 20% of the length of the coupling element, although in other embodiments this could be between 1% to 60% of the length of the coupling element, more preferably between 10 to 40% and most preferably between 10 to 30%.

In one example, for a coupling element having a length of around 2 millimeters, the hinge could have a length of around 0.4 millimeters.

The hinge, by being of limited longitudinal length, enables the coupling element to retain substantially the entirety of its longitudinal strength and thus for the stented structure to retain substantially all of its longitudinal stability.

The hinge could be located at one end of its associated coupling element, for example adjacent the stent ring, while in other embodiments the hinge could be located in an intermediate position along the length of the coupling element, such as in the region of its centre.

The coupling elements, which are preferably tie bars, advantageously extend substantially parallel to the longitudinal axis of the stented structure.

The medical device could be a stent, a stent graft, a vena cava filter, an occlusion device or any other implantable medical device.

According to another aspect of the present invention, there is provided a method of making a conformable medical device provided with a shape memory stented structure formed of a plurality of stent rings coupled to one another by one or more coupling elements, wherein one or more hinges are formed in the or at least one of said coupling elements by heat treating a part of the or said at least one coupling element so as to raise the transition temperature of said part.

DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
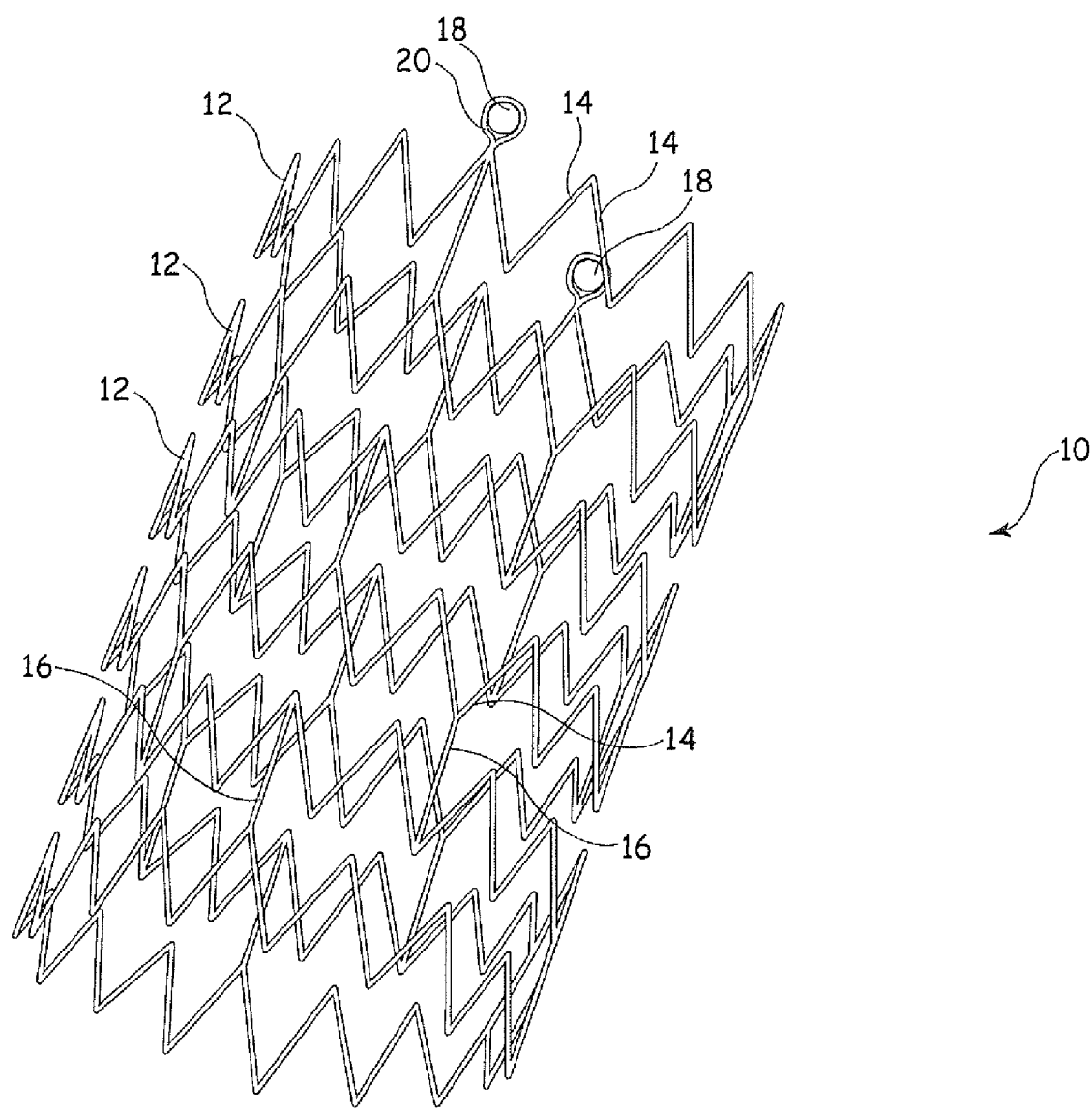
FIG. 1 is a perspective view of an embodiment of stent.

Referring to FIG. 1, there is shown a perspective view of an example of stent structure which is provided with a plurality of stent rings 12 each formed of a series of struts 14 which are coupled to one another at their extremities in a zig-zag fashion. The struts 14 are substantially straight along their length, although could have a slight curvature if desired or appropriate.

The stent rings 12 are coupled to one another by a series of tie bars 16, which are typically located between the apex of two struts 14 of one stent ring 12 and the valley of two struts 14 of the adjacent stent ring 12. The tie bars 16 are typically evenly spread around the stent structure so as to link the various stent rings 12 together mechanically and yet provide the stent 10 with a degree of flexibility to enable this to be fitted to a curved lumen of a patient's vasculature.

In this particular example, first and second radiopaque markers 18 are provided at the extremity of the stent 10 and there would typically be provided equivalent radiopaque markers at the other end of the stent. These markers 18 are typically located on or within an appropriate holder 20 which is integrally formed with the end-most stent 12 of the stent assembly 10.

The stent 10 will have a length determined by the particular medical application and could typically be from around 5 to around 20 cm in length. Equally, stent 10 could have a diameter dependent upon a particular medical application, from a few millimeters to a few tens of millimeters. The design of the stent 10 is also of a type suitable for intra-cranial applications.

The stent 10 could be of a balloon-expandable type and made from a material which can deform plastically. In other embodiments, the stent 10 is made of a shape memory material, such as Nitinol, or other shape memory alloy, metal or polymer. When made of a shape memory material, as is well known in the art, the stent 10 will expand once it is released from the constraining mechanisms provided on the delivery introducer. A self-expandable stent 10 has the advantage of being able to press continuously against the vessel walls to ensure that it remains correctly positioned within the vessel and maintains an opening force on the vessel walls. The stent 10 is also conformable in its longitudinal direction (that is a direction substantially transverse to the plane of the individual stent rings 12) and for this purpose the strut 16 as well as the stent rings 12 are preferably conformable. This is generally as a result of the flexibility of the stent 10.

It will be appreciated by the person skilled in the art that, particularly in the case of stents which are made of a material having spring-like characteristics in such as of a shape memory material which transitions to its memorised shape or of a spring material such as spring steel or the like, the stent 10 will tend to straighten in the lumen in order to seek to return to its non-biased condition. As a result of this, the stent 10 will continuously apply a straightening force against the walls of the lumen. In the case of a strong lumen, such as an aortic vessel, such straightening force is generally not an issue. However, it can become more relevant in more delicate lumens, such as much smaller lumens and cerebral vessels.

Figure 2:
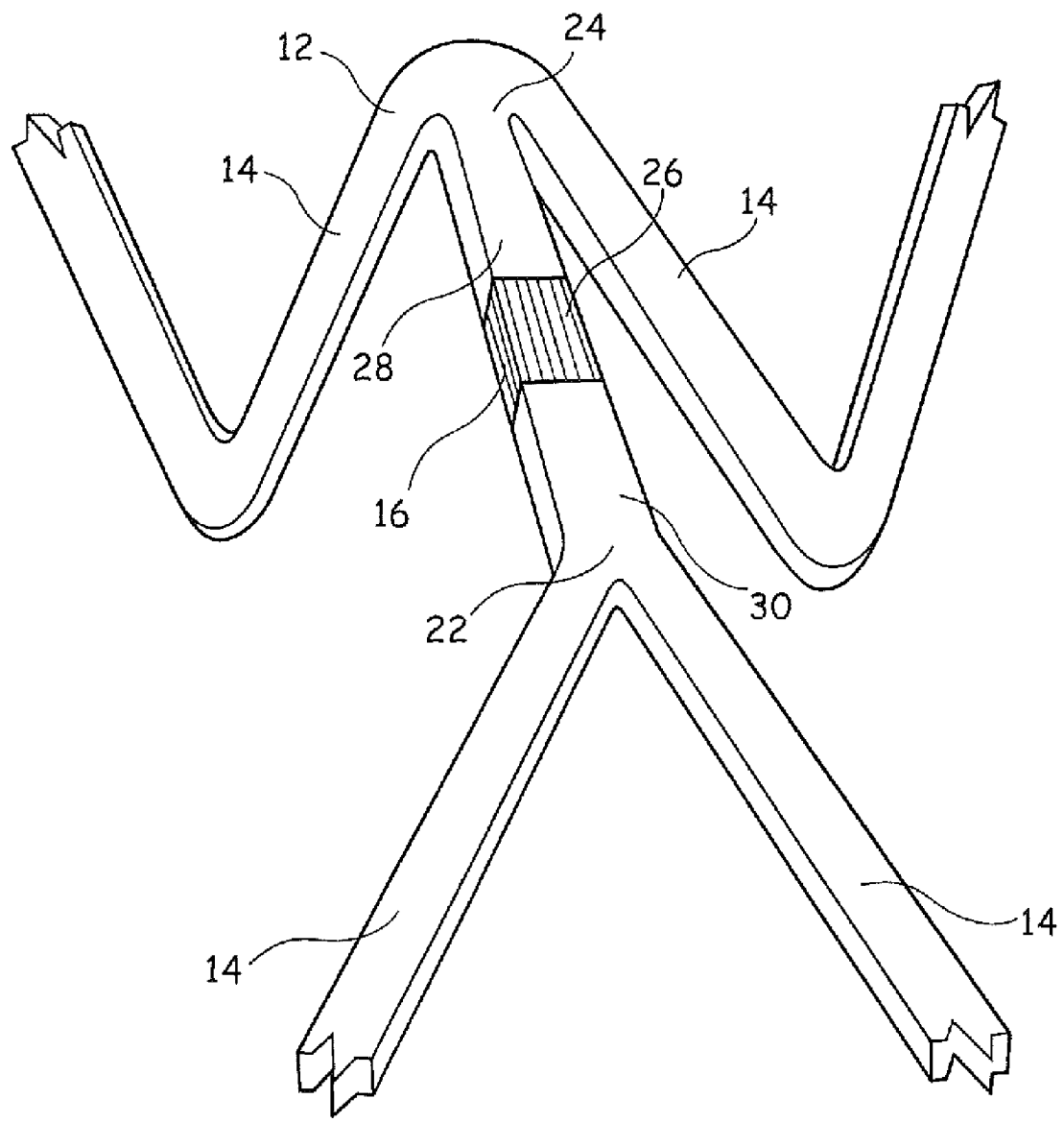
FIG. 2 is an enlarged perspective view of a part of the stent of FIG. 1.

FIG. 2 shows an enlarged view of a part of the stent assembly 10 of FIG. 1. More particularly, FIG. 2 shows parts of two stent rings 12 at the point at which they are coupled together by a tie bar 16. In this particular view, the lower stent ring 12 is coupled at the apex 22 of two struts 14, while the upper stent ring 12 (as seen in FIG. 2) is coupled to the tie bar 16 at a valley 24 between two stent struts 14. The tie bar 16 is provided with a hinged zone 26, which in this embodiment is located approximately half-way along the length of the tie bar 16, leaving two tie bar sections 28, 30 either side of the hinge section 26. In other embodiments, the hinge 26 could be located at an end of the tie bar 16, for example adjacent the valley 24 or adjacent the peak 22. In such circumstance, the tie bar 16 may be formed simply of the hinge 26 and a single portion of tie bar 28 or 30.

The position of the hinge 26 along the tie bar 16 is not considered critical, although it is preferred that it is at or proximate the mid-point of the tie bar 16.

The hinge 26 may have a length which is anything from around 1 to around 60% of the overall length of the tie bar 16 (that is, in the embodiment of FIG. 2, the sections 28, 30 and the hinge 26 combined). More preferably, the hinge 26 may be from around 10% to around 40% or around 10% to around 30% of the length of the tie bar 16. In the preferred embodiment it is around 20% of this length.

The hinge section 26 has a flexibility which is substantially greater than the flexibility of the tie bar sections 28/30 and of the struts 14 forming the stent rings 12. The difference in flexibilities between the hinge section 26 and the remainder of the tie bar 16 is such that the remaining portions of the tie bar 16 (in the embodiment of FIG. 2 the sections 28 and 30) are able to pivot about the hinge section 26 without any substantial return force being imparted upon the sections 28 and 30 which would cause sections 28 and 30 to be bent to any noticeable degree. In other words, it is preferred that the hinge section 26 acts as a conventional hinge to allow pivoting of the sections 28, 30 rather than forcing these to curve as a result of stiffness of the coupling between the two sections 28, 30. This characteristic of the hinge 26 enables the various parts of the stent 10 (in particular adjacent stent rings 12) to be pivoted about the hinges 26 in the tie bars 16 and thus for the stent 10 as a whole to be able to be conformed in to a curved configuration. This curvature of the stent structure occurs with substantially no return force generated by the hinged sections 26 seeking to straighten, or at least with only a very substantially reduced force compared to a conventional stent structure which is not provided with hinged regions 26. In addition to this, it will be apparent that the tie bars 16 still retain their rigidity over a substantial part of their length (the portions 28 and/or 30) and thus retains a significant support in the longitudinal direction between two adjacent stent rings 12. This differs from structures which use wholly flexible tie bars 16 or entire regions (including stent rings) of stent of softer material and which thus lose longitudinal stability and strength of the stent structure.

In any embodiment, a stent 10 is provided with a plurality of tie bars 16 having a length in the region of 2 mm and hinges 26 of a length of around 0.4 mm. It will be appreciated that a hinge of such dimensions would have little effect on the support characteristics in the longitudinal direction of the tie bar 16.

In the preferred embodiment, hinge regions 26 are formed in the tie bars 16 by heat treating the shape memory material in the zone of the hinge 26, in a manner well known in the art (by laser heating for example), so as to cause the region of the hinge 26 to have an elevated transition temperature, preferably in the region of 40 to 60° C. This contrasts with the transition temperature of the portions 28 and/or 30 of the tie bar 16, as well as of the stent rings 12, which typically would be in the region of 25 to 30° C. A higher transition temperature, substantially above normal body temperature, results in the hinges 26 remaining in the martensitic state when the device is in a patient. In this state, the shape memory material forming the stent 10 (which preferably is the same material throughout the entirety of the stent 10, including the stent rings and tie bars) will deform pseudo plastically at normal body temperature and will thus produce virtually no straightening force once so deformed. As a result, the stent 10 can be curved to suit the curvature of a lumen within which a stent 10 is positioned and will not seek to straighten that lumen, as would be the case with a conventional stent or stented structure.

It will be appreciated that the preferred embodiment provides a hinged section 26 formed by modification of the characteristics of the shape memory material of the stent 10. In other embodiments, the hinge 26 could be formed of a different material, for example a material not having shape memory characteristics and bonded, welded or otherwise attached to or integrally formed with the sections 28, 30 of the tie bar element 16. Such a solution, however, is more complex to manufacture and is therefore less preferable than the preferred embodiment described above.

Even though the preferred embodiment described above is directed to a stent formed of shape memory material, the teachings herein are equally applicable to stents which are expandable by a separate mechanism, such as by balloon.

In the preferred embodiment, all of the tie bars 16 are provided with hinge sections 26, although it is envisaged that in some embodiments only some of the tie bars 16 would be provided with hinges 26. Providing some hinges within the tie bars 16 will substantially reduce the force produced by the stent 10 in seeking to return to its unbiased configuration (typically straight).

FIG. 2 shows an embodiment in which the hinge section 26 is located substantially mid-way along the tie bar 16, forming two substantial equal tie bar section 28, 30 either side. In other embodiments the hinge 26 could be located in other positions along the tie bar 16, such as close to or at the valley 24 or close to or at the peak 30.

Similarly, although the preferred embodiment includes a single hinge 26 in a tie bar 16, it is envisaged that there may be provided more than one hinge 26 in a tie bar 16, for example two hinges, one at either end of the tie bar. Similarly, in some embodiments it may be desired to provide hinges 26 within the struts 14 forming the stent rings 12.

The preferred embodiments described above are related to stents. However, the teachings herein are not limited to stents and are equally applicable to other stented structures, such as stent grafts, vena cava filters, occlusion devices and other implantable medical devices.

What is claimed is:

1. An implantable medical device including a stented structure formed of a plurality of stent rings coupled together by one or more coupling elements, each coupling element extending from one stent ring to another stent ring, the coupled stent rings extending in at least one longitudinal direction, the or at least one of the coupling elements having a longitudinal axis that extends substantially parallel to the longitudinal axis of the stented structure along an entire length of each coupling element when the stented structure is expanded and being hinged along only a portion of each coupling element to allow for said coupled stent rings to pivot around the hinge or hinges so as to flex the stented structure in said longitudinal direction; the stented structure being made of shape memory material having a first transition temperature, the hinge or hinges being heat treated zones with a transition temperature higher than the first transition temperature so as to provide zones of increased flexibility within the stented structure.

2. An implantable medical device according to claim 1, wherein the stented structure is formed from Nitinol.

3. An implantable medical device according to claim 1, wherein the or each hinge represents between 1% to 60% of the length of the coupling element.

4. An implantable medical device according to claim 3, wherein the or each hinge is about 10% to about 40% of the length of the associated coupling element.

5. An implantable medical device according to claim 4, wherein the or each hinge is around 20% of the length of its coupling element.

6. An implantable medical device according to claim 1, wherein the coupling elements are tie bars.

7. An implantable medical device according to claim 1, wherein the device is a stent, a stent graft, a vena cava filter or an occlusion device.

8. An implantable medical device according to claim 1, wherein the stented structure is formed from Nitinol, the or each hinge represents between 1% to 60% of the length of the coupling element, the device is a stent, a stent graft, a vena cava filter or an occlusion device, the coupling elements are tie bars, and the or each hinge has a transition temperature above 40° C.

9. An implantable medical device according to claim 8, wherein the or each hinge is about 10% to about 40% of the length of the associated coupling element, and the or each hinge has a transition temperature above 60° C.

10. An implantable medical device according to claim 9, wherein the or each hinge is around 20% of the length of its coupling element.

11. A method of making a conformable medical device provided with a shape memory stented structure formed of a plurality of stent rings coupled to one another by one or more coupling elements such that the stent rings extend in at least one longitudinal direction and each coupling element extends from one stent ring to another stent ring, the or each coupling element having a longitudinal axis that extends substantially parallel to the longitudinal axis of the stented structure along an entire length of each coupling element when the stented structure is expanded, wherein one or more hinges are formed in the or at least one of said coupling elements along only a portion of each coupling element by heat treating the portion of the or said at least one coupling element so as to raise the transition temperature of said portion.

12. A method of making a conformable medical device according to claim 11, wherein the at least one hinge has a transition temperature above 40° C.

13. A method of making a conformable medical device according to claim 12, wherein the at least one hinge has a transition temperature above 60° C.

14. A method of making a conformable medical device according to claim 11, wherein the stented structure is formed from Nitinol, the at least one hinge represents between 1% to 60% of the length of the coupling element, the device is a stent, a stent graft, a vena cava filter or an occlusion device, the coupling elements are tie bars, and the at least one hinge has a transition temperature above 40° C.

15. A method of making a conformable medical device according to claim 14, wherein the at least one hinge is about 10% to about 40% of the length of the associated coupling element, and the at least one hinge has a transition temperature above 60° C.

16. A method of making a conformable medical device according to claim 15, wherein the at least one hinge is around 20% of the length of its coupling element.

* * * * *